US009970860B2

(12) United States Patent
Murayama et al.

(10) Patent No.: US 9,970,860 B2
(45) Date of Patent: May 15, 2018

(54) POLARIZATION INSPECTION DEVICE

(71) Applicant: YOKOGAWA ELECTRIC CORPORATION, Tokyo (JP)

(72) Inventors: Kodai Murayama, Tokyo (JP); Tomohito Nohno, Tokyo (JP); Toyoaki Hamaguchi, Tokyo (JP); Soukichi Funazaki, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days. days.

(21) Appl. No.: 15/381,167

(22) Filed: Dec. 16, 2016

(65) Prior Publication Data
US 2017/0176323 A1 Jun. 22, 2017

(30) Foreign Application Priority Data

Dec. 21, 2015 (JP) .................................. 2015-248976

(51) Int. Cl.
*G01J 4/00* (2006.01)
*G01N 21/21* (2006.01)
*G01N 21/88* (2006.01)
*G01N 33/00* (2006.01)
*G02B 5/04* (2006.01)
*G01N 21/47* (2006.01)

(52) U.S. Cl.
CPC ............ *G01N 21/21* (2013.01); *G01N 21/211* (2013.01); *G01N 21/8806* (2013.01); *G01N 33/00* (2013.01); *G02B 5/04* (2013.01); *G01N 2021/4792* (2013.01); *G01N 2021/8848* (2013.01); *G01N 2033/0096* (2013.01)

(58) Field of Classification Search
CPC .... G01N 21/21; G01N 21/8422; G01N 21/88; G01N 2021/8848; G01B 11/0641; G01J 4/04
See application file for complete search history.

(56) References Cited

U.S. PATENT DOCUMENTS 4,872,758 A * 10/1989 Miyazaki ............. G01N 21/211
356/369
5,311,285 A * 5/1994 Oshige .................. G01B 11/065
356/367
5,835,220 A * 11/1998 Kazama ............... G01N 21/211
356/237.2

(Continued)

FOREIGN PATENT DOCUMENTS

JP 9-178666 A 7/1997
JP 2004-212979 A 7/2004

(Continued)

*Primary Examiner* — Kara E Geisel
*Assistant Examiner* — Maurice Smith
(74) *Attorney, Agent, or Firm* — Sughrue Mion, PLLC

(57) ABSTRACT

A polarization inspector for inspecting an inspection target, the polarization inspector having a polarization divider for spatially dividing at least a reflected beam of light from the inspection target by irradiating an illumination beam into divided beams of lights mutually different in polarization direction; one or more optical receivers for receiving the divided beams of lights and generating an image signal based on the divided beams of lights; and a processor for calculating at least one of an elliptical azimuth angle, a polarization degree and a polarization component intensity from the image signal.

18 Claims, 11 Drawing Sheets

(56) References Cited

U.S. PATENT DOCUMENTS

| | | | | |
|---|---|---|---|---|
| 6,134,011 | A * | 10/2000 | Klein | G01N 21/211 250/225 |
| 7,079,247 | B2 * | 7/2006 | Shribak | G01J 4/04 356/364 |
| 2001/0024277 | A1 * | 9/2001 | Hirosawa | G01N 21/211 356/369 |
| 2004/0156134 | A1 * | 8/2004 | Furuki | G02B 5/04 359/883 |
| 2006/0250611 | A1 * | 11/2006 | Velidandla | G01B 11/303 356/237.2 |
| 2008/0031117 | A1 * | 2/2008 | Li | G03H 1/02 369/103 |
| 2008/0198380 | A1 | 8/2008 | Straaijer et al. | |
| 2011/0102793 | A1 | 5/2011 | Straaijer | |
| 2013/0033707 | A1 * | 2/2013 | Yamada | G01J 4/04 356/364 |
| 2015/0346083 | A1 | 12/2015 | Matsumoto et al. | |
| 2016/0047987 | A1 * | 2/2016 | Du | G02B 6/2746 359/484.05 |

FOREIGN PATENT DOCUMENTS

| | | |
|---|---|---|
| JP | 2007-322316 A | 12/2007 |
| JP | 2015227827 A | 12/2015 |

* cited by examiner

POLARIZATION INSPECTION DEVICE

BACKGROUND OF THE INVENTION

Field of the Invention

The present invention relates to an polarization inspection device (inspector) for inspecting an inspection target based on the polarization condition of light via the inspection target.

Priority is claimed on Japanese Patent Application No. 2015-248976, filed on Dec. 21, 2015, the contents of which are incorporated herein by reference.

Description of Related Art

The polarization inspector irradiates inspection target with light in specific polarization condition, thereby receives plural reflected lights having different polarization conditions each other from the inspection target, and inspects the inspection target using the reflected light. The light in the polarization condition is, for example, a linearly polarized beam of light or a circularly polarized beam of light. The reflected light may be a transmitted light. Such the polarization inspector is used to inspect defect on the surface and the inside of the manufactured product. The defects may be dusts, scratches, irregularities.

In recent years, diversity of functions and structures of the organic material is paid attention, and various devices used organic materials have been actively developed and studied. The polarization inspector may be used to inspect quality of a thin film (an organic thin film) which is used the organic material. The polarization inspector, for example, inspects an polarization film which is used for an organic thin-film solar cell, an organic EL (Electro Luminescence) display, a liquid crystal display or the like, and RFID (Radio Frequency IDentification) tag which is used an organic semiconductor or the like.

Patent References 1 (Japanese Patent Application Publication No. 1997-178666), and Patent References 2 (Japanese Patent Application Publication No. 2007-322316) listed below discloses an example of a polarization inspector in the prior art. Specifically, Patent Reference 1 listed below discloses the polarization inspector. The polarization inspector divides the reflected light reflected by the surface of the steel sheet by using a beam splitter, and to measure three type polarizations which are different from each other by using a linear array camera. The polarization inspector obtains ellipso parameter of the reflected light, and determines the type and the grade of surface flaws on the inspection target. Further, Patent Reference 2 listed below discloses a polarization inspector. The polarization inspector disclosed in Patent Reference 2 makes it possible to select the plural linearly polarized beams of lights which are most suitable for the inspection and to irradiate the inspection target with the linearly polarized beam of light, in order to solve the problem that it is difficult to find defects due to a change of the reflection surface or the like due to the movement of the inspection target.

DISCLOSURE OF THE INVENTION

Problems to be Solved by the Invention

The thin film such as the organic thin film described above can be fabricated by using the continuous production method called the roll-to-roll. Here, the roll-to-roll is a kind of the continuous production method. The roll-to-roll continuously coats the film with the organic material while pulling the film wound like roll to form the organic thin film, and then winds the film coated with the organic thin film to the roll again. The inspection of the organic thin film manufactured by using such method is generally performed in a condition that the organic thin film which is the inspection target is moving.

By using the above-noted polarization inspector disclosed in Patent References 1 and 2, it is considered that the inspection target can be inspected even when the inspection target is moving. However, the polarization inspector disclosed in the above-mentioned Patent Reference 1 is suitable for inspecting the surface flaws of the inspection target of which surface reflectivity is high such as a steel plate or the like, and is not suitable for inspecting the film quality of the organic thin film. Here, the film quality of the organic thin film depends on quality of the orientation of the molecular material. Patent Reference 2 described above also describes the similar matters.

Furthermore, there is a rotating analyzer as a general method for detecting the polarization condition of the light. The rotating analyzer provides an analyzer such as a polarizing plate on a light receiving side. Then, the rotating analyzer detects changing of light amount of the light obtained from the analyzer while rotating the analyzer, and to detect the polarization condition of the light. It is considered that the polarization inspector using the rotating analyzer can satisfactorily inspect the film quality of the organic thin film even if the inspection target is the organic thin film.

However, the polarization inspector using the rotating analyzer needs to detect the changing of the light amount while rotating the analyzer, and thereby there is a problem that it is required much time for the inspection. Further, it has a problem that utilization efficiency of the light is poor since the polarization inspector receives only the light transmitted through the analyzer. Thereby, it needs long measurement time when the light amount is small. Therefore, the polarization inspector using the rotating analyzer has a problem that it is difficult to inspect the inspection target in a condition which the inspection target is moving. Further, the polarization inspector using the rotating analyzer needs a mechanism for rotating the analyzer, and thereby there is also a problem that the device configuration becomes large.

The present invention is a small sized and a low-cost polarization inspector which is capable of inspecting the inspection target in a short time.

SUMMARY

One aspect of the present invention is a polarization inspector for inspecting an inspection target, the polarization inspector includes: a polarization divider configured to spatially divide at least a reflected beam of light from the inspection target by irradiating an illumination beam into divided beams of lights mutually different in polarization direction; one or more optical receivers configured to receive the divided beams of lights and to generate an image signal based on the divided beams of lights; and a processor configured to calculate at least one of an elliptical azimuth angle, a polarization degree and a polarization component intensity from the image signal.

In another aspect of the present invention of the polarization inspector, the polarization divider further includes: a beam splitter configured to split at least the reflected beam of light having the polarization direction obtained from the inspection target into a first split beam of light and a second split beam of light; a wavelength device configured to rotate by 45 degrees either one of the first split beam of light or the second split beam of light to differentiate in polarization direction by 45 degrees between the first split beam of light and the second split beam of light; and a polarization dividing element configured to obtain the first split beam or the second split beam which do not transmitted through the wavelength device and the first split beam or the second split beam which transmitted through the wavelength device among the first split beam and the second split beam, to divide each of the first split beam and the second split beam into plural divided lights of which the polarization directions are mutually perpendicular.

In another aspect of the present invention of the polarization inspector, the polarization dividing element includes: a first optical member that surfaces of a first trapezoidal prism, a first diamond-shaped prism, and a first triangular prism are mutually bonded; and a second optical member that surfaces of a second trapezoidal prism, a second diamond-shaped prism, and a second triangular prism are mutually bonded; wherein the first optical member and the second optical member are bonded that the surface of the first diamond-shaped prism of the first optical member and the surface of the second diamond-shaped prism of the second optical member are perpendicular.

In another aspect of the present invention of the polarization inspector, the surface of which the first trapezoidal prism and the first diamond-shaped prism are bonded is a translucent surface, and each the surface of which the first diamond-shaped prism and the first triangular prism of the first optical member are bonded, the surface of which the second trapezoidal prism and the second diamond-shaped prism of the second optical member are bonded, and the surface of which the second diamond-shaped prism and the second triangular prism of the second optical member are bonded is a total reflection surface.

In another aspect of the present invention of the polarization inspector, the optical receiver includes an image sensor configured to independently obtain each of the plural divided beams of lights which are divided by the polarization divider in mutually different areas of an imaging surface.

In another aspect of the present invention of the polarization inspector, the polarization divider includes: a beam splitter configured to split at least the reflected beam of light obtained from the inspection target into a first split beam of light and a second split beam of light which proceed to the mutually different directions; a first divider configured to divide the first split beam of light into plural divided beams of lights of which the polarization directions are mutually perpendicular; and a second divider configured to divide the second split beam of light into plural divided beams of lights of which the polarization directions are mutually perpendicular and each of the polarization directions form 45 degrees to the polarization directions of the divided beams of lights divided by the first divider.

In another aspect of the present invention of the polarization inspector, either the first divider or the second divider includes a polarization dividing element configured to divide either the first split beam of light or the second split beam of light into the plural divided beams of lights of which the polarization directions are mutually perpendicular; another one of the first divider or the second divider includes a wavelength device configured to rotate by 45 degrees another one of the polarization directions of the first split beam of light or the second split beam of light and a polarization dividing element configured to divide another one of the first split beam of light or the second split beam of light which transmitted through the wavelength device into the plural divided beams of lights of which the polarization directions are mutually perpendicular.

In another aspect of the present invention of the polarization inspector, each the first divider and the second divider includes a polarization dividing element configured to divide either the first split beam of light or the second split beam of light into the plural divided beams of lights of which the polarization directions are mutually perpendicular; the plural polarization dividing elements are configured to arrange that the one polarization dividing element forms 45 degrees to the crystal axis direction of the first split beam of light or the second split beam of light to the other polarization dividing element.

In another aspect of the present invention of the polarization inspector, the optical receiver includes: a first optical receiving element configured to independently obtain the plural respective divided beams of lights divided by the first divider in the mutually different areas of the imaging surface; and a second optical receiving element configured to independently obtain the plural respective divided beams of lights divided by the second divider in the mutually different areas of the imaging surface.

In another aspect of the present invention of the polarization inspector, the optical receiver includes optical receiving elements that are arranged in accordance with the plural respective divided beams of lights divided by the polarization divider.

In another aspect of the present invention of the polarization inspector, the polarization inspector includes an irradiator configured to irradiate an illumination beam of light to the inspection target; wherein the irradiator includes a wavelength filter configured to pass only a light having a predefined wavelength or a light of a predefined wavelength band.

In another aspect of the present invention of the polarization inspector, the polarization divider is configured to spatially divide the reflected beam of light of which the illumination beam of light is reflected by the inspection target or the transmitted beam of light of which the illumination beam of light is transmitted through the inspection target into the plural divided beams of lights of which the polarization directions are mutually different.

The polarization inspector of the present invention is capable of irradiating the inspection target with the light of which the polarization condition is known. The polarization inspector of the present invention is capable of spatially dividing the light obtained from the inspection target into plural lights which the polarization direction is mutually different. The polarization inspector of the present invention is capable of acquiring at least one of elliptical azimuth angle, polarization degree, and polarization component intensity by using the reception signal independently received the divided lights. Thereby, the polarization inspector of the present invention determines the quality of the inspection target. Therefore, the inspection of the inspection target can be carried out by using the small sized device, and in a short time and at low cost.

DETAILED DESCRIPTION OF THE PREFERRED EMBODIMENTS

Hereinafter, a detailed description of a polarization inspector according to an embodiment of the present invention will be described with reference to the drawings.

<First Embodiment>

Figure 1:
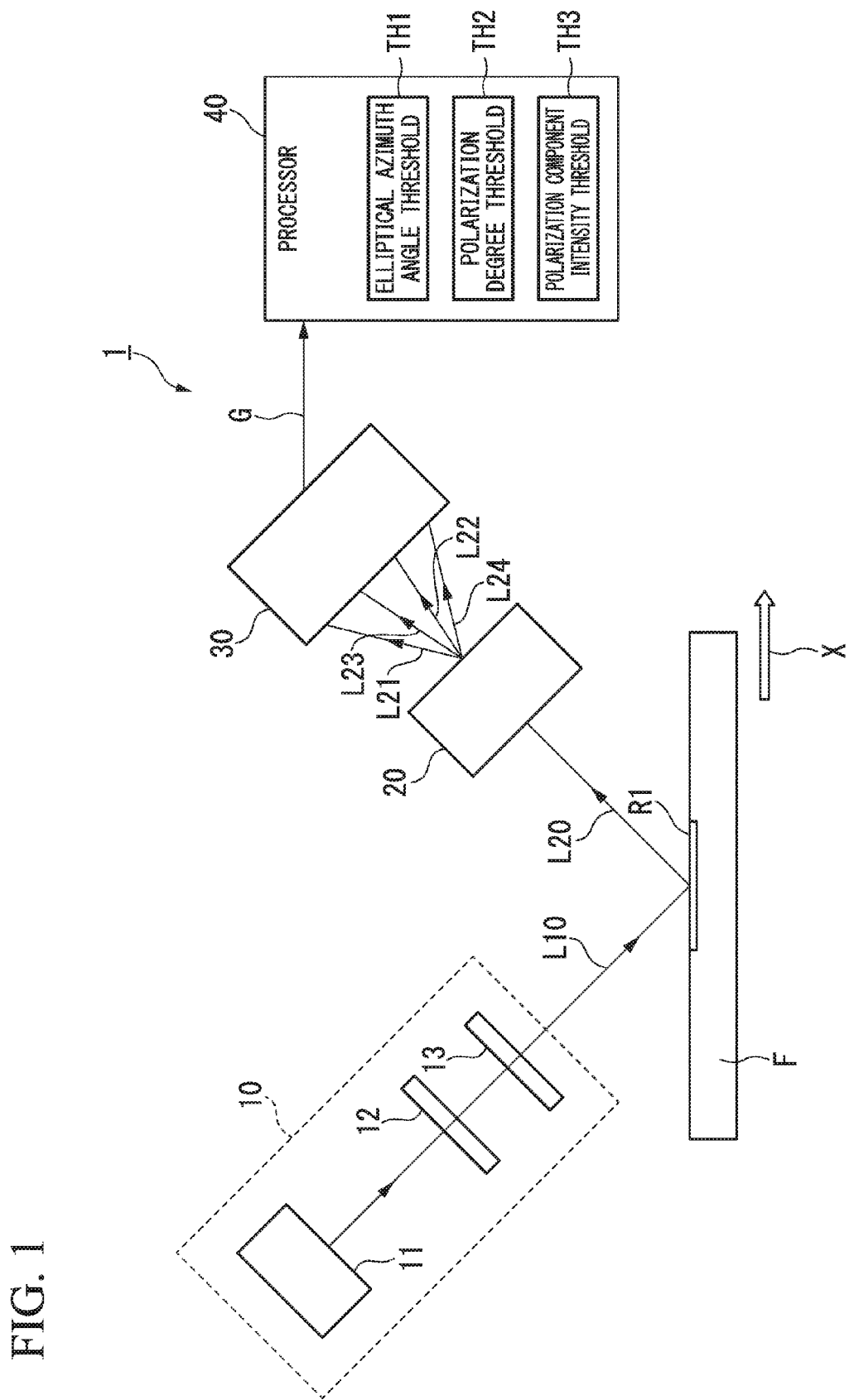
FIG. 1 is a block diagram showing a main construction of a polarization inspector according to a first embodiment of the present invention.

FIG. 1 is a block diagram showing a main construction of a polarization inspector according to a first embodiment of the present invention. A polarization inspector 1 according to the present embodiment includes an irradiator 10, a polarization divider (dividor) 20, an optical receiver 30 and a processor 40, as shown in FIG. 1. The polarization inspector 1 inspects film quality of an inspection target F which is conveyed toward a conveying direction X. Specifically, the polarization inspector 1 irradiates the inspection target F with an illumination light L10 of which a polarization condition is already known. The polarization inspector 1 spatially divide a reflected light L20 obtained from the inspection target F into plural divided lights L21 to L24 which mutually directs polarizations which are different from each other. Then, the polarization inspector 1 independently receives the divided lights L21 to L24, and to inspect the film quality of the inspection target F by using the lights. The polarization inspector 1 uses a reflection system.

Here, the inspection target F is, for example, an organic thin film. The inspection target F may be in a condition before being formed as a device. Further, the inspection target F may be in a condition after being formed as a device. The organic thin film may be, for example, an organic thin-film solar cell, an organic EL display, a polarizing film used for a liquid crystal display or the like. The organic thin film may be a RFID tag or the like used an organic semiconductor. In the following description, it is referred to as a "width direction Y" which is perpendicular to the conveying direction X of the inspection target F and is included in the plane of the inspection target F.

The irradiator 10 includes a light source 11, a polarizer 12, and a quarter-wave plate 13, and may be disposed on the surface side of the inspection target F. The irradiator 10 irradiates the inspection area R1 set on the inspection target F with the illumination light L10 of which the polarization condition is already known. Here, the inspection area R1 set on the inspection target F is, for example, a rectangular shaped area that the length of the conveying direction X and the length of the width direction Y are set in several cm to some ten cm. The size of the inspection area R1 is set appropriately according to the size of the inspection target F.

The light source 11 includes, for example, a LED (Light Emitting Diode) and a LD (Laser Diode) and the like, and emits light of which a wavelength and a polarization condition is already known. The wavelength of the light emitted from the light source 11 is appropriately set depending on optical characteristics of the inspection target F and a structure of the inspection target F. The wavelength of the light emitted from the light source 11 may be a wavelength in the visible light area, and may be a wavelength other than the visible light area such as a wavelength of an infrared light area. Further, the polarization condition of the light emitted from the light source 11 may be a linearly polarized beam of light, a circularly polarized beam of light, an elliptically polarized beam of light, and a random.

The polarizer 12 changes the polarization condition of the light emitted from the light source 11 into the predefined polarization condition. For example, the polarizer 12 changes the polarization condition of the light emitted from the light source 11 into the linearly polarized beam of light of which the vibration direction of the electric field is a direction perpendicular to the paper surface. The quarter-wave plate 13 changes the polarization condition of the light transmitted through the polarizer 12. For example, the quarter-wave plate 13 changes the polarization condition of light changed to the linearly polarized beam of light by the polarizer 12 into the circularly polarized beam of light. The light transmitted through the quarter-wave plate 13 irradiates the inspection area R1 set on the inspection target F as the illuminating light L10. That is, in this embodiment, the illumination light L10 which is the circularly polarized beam of light irradiates the inspection area R1 of the inspection target F.

Incidentally, since the illumination light L10 of which the polarization condition is already known is necessary to be irradiated on the inspection target F, the polarizer 12 of the irradiator 10 of the polarization inspector 1 and the quarter-wave plate 13 of the irradiator 10 of the polarization inspector 1 can be omitted depending on the polarization condition of the illumination light L10 which is to be irradiated to the inspection target F. Further, the illumination light L10 irradiated to the inspection area R1 of the inspection target F from the irradiator 10 may be a parallel light, and also a condensed light. If the illumination light L10 irradiated onto the inspection area R1 is the condensed light, a lens for focusing the illumination light L10 onto the inspection area R1 which is set on the inspection target F is provided in the irradiator 10.

The polarization divider 20 is disposed on the surface side of the inspection target F. Then, the polarization divider 20 spatially divides the reflected light L20 reflected by the inspection target F into the plural divided lights L21 to L24 of which the polarization directions are mutually different. Specifically, the polarization divider 20 divides the reflected light L20 reflected by the inspection target F into a linearly polarized light L21 (the divided lights L21) of which the vibration direction of the electric field is 0 degree, a linearly polarized light L22 (the divided lights L22) of which the vibration direction of the electric field is 45 degrees, a linearly polarized light L23 (the divided lights L23) of which the vibration direction of the electric field is 90 degrees, and a linearly polarized light L24 (the divided lights L24) of which the vibration direction of the electric field is 135 degrees. Incidentally, the vibration direction of the divided lights L21 to L24 in the electric field is represented by an angle in a plane which is perpendicular to the progressing direction of the divided lights L21 to L24. Here, the direction which is perpendicular to the incident surface of the illumination light L10 to the inspection target F is 0 degree. That is, the direction which is perpendicular to the paper plane of FIG. 1 is 0 degree.

Figure 2:
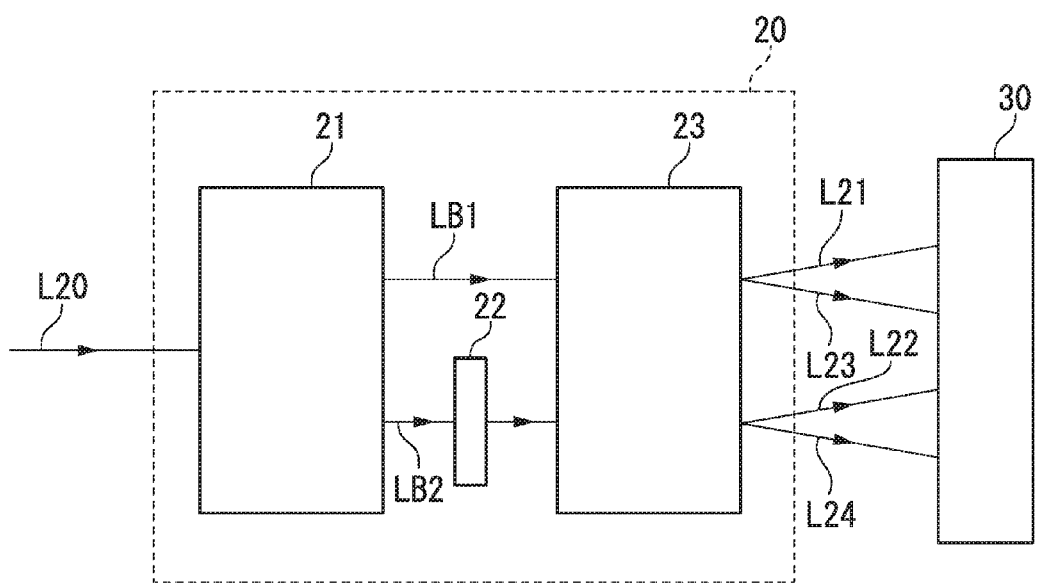
FIG. 2 is a block diagram showing a construction of a polarization divider provided on the polarization inspector according to the first embodiment of the present invention.

FIG. 2 is a block diagram showing a construction of a polarization divider provided on the polarization inspector according to the first embodiment of the present invention. As shown in FIG. 2, the polarization divider (dividor) 20 includes a beam splitter 21, a half-wavelength plate 22 (a wavelength plate, or a wavelength device), and the polarization dividing element 23. The beam splitter 21 splits a reflected light L20 obtained from the inspection target F into a split beam LB1 (first split beam) and a split beam LB2 (second split beam) which are mutually parallel. The details of the beam splitter 21 will be described later. The half-wavelength plate 22 is disposed on the optical path of the split beam LB2, and rotates by 45 degrees the polarization direction of the split beam LB2. Incidentally, the half-wavelength plate 22 may be disposed on the optical path of the split beam LB1 instead of the optical path of the split beam LB2.

The polarization dividing element 23, for example, includes a Wollaston Prism, and is disposed on the optical path of the split beam LB2 transmitted through the split beam LB1 and the half-wavelength plate 22, and then divides the split beam LB1 and the split beam LB2 into plural divided lights of which the polarization directions are mutually perpendicular. Specifically, the polarization dividing element 23 divides the split beam LB1 into the linearly polarized light L21 of which the vibration direction of the electric field is 0 degree and the linearly polarized light L23 of which the vibration direction of the electric field is 90 degrees. In addition, the polarization dividing element 23 divides the split beam LB2 into the linearly polarized light L22 of which the vibration direction of the electric field is 45 degrees and the linearly polarized light L24 of which the vibration direction of the electric field is 135 degrees.

In order to equalize the optical path lengths of the split beam LB1 and the split beam LB2, it may dispose an optical element (e.g., glass) which may be same thickness as the half-wavelength plate 22 on the optical path of the split beam LB1. The polarization divider 20 may be attached and integrated by the beam splitter 21, a half-wavelength plate 22, and the polarization dividing element 23 (and further the above optical element). Since these elements are integrated, the polarization divider 20 can be more miniaturized.

Figure 3:
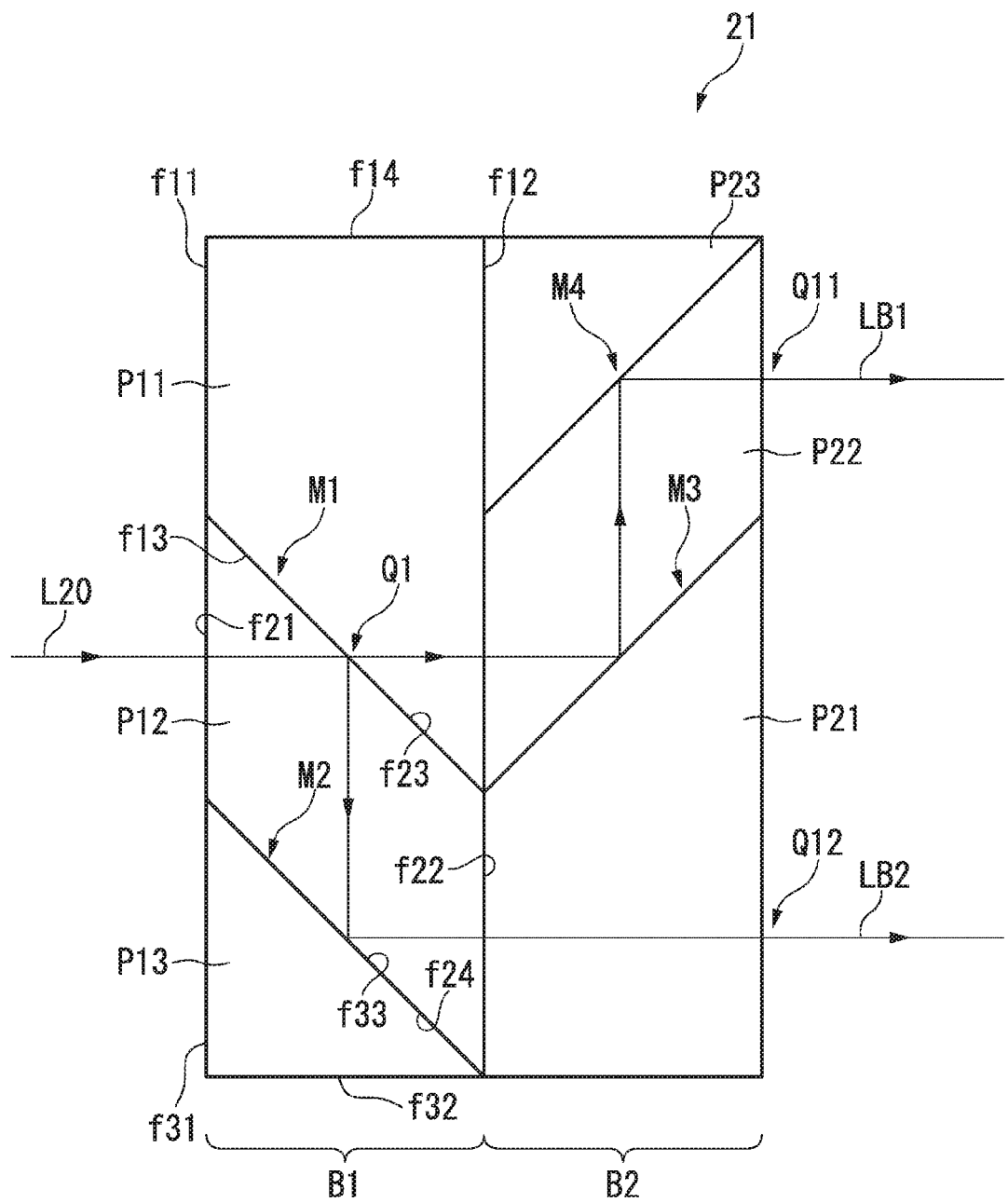
FIG. 3 is a diagram showing a construction of a beam splitter provided in the polarization divider according to the first embodiment of the present invention.

FIG. 3 is a diagram showing a construction of a beam splitter provided in the polarization divider according to the first embodiment of the present invention. As shown in FIG. 3, the beam splitter 21 includes an optical member B1 (a first optical member) and an optical member B2 (a second optical member). The optical member B1 includes a trapezoidal prism P11 (a first trapezoidal prism), a diamond-shaped prism P12 (a first diamond-shaped prism), and a triangular prism P13 (a first triangular prism). The optical member B2 includes a trapezoidal prism P21 (a second trapezoidal prism), a diamond-shaped prism P22 (a second diamond-shaped prism), and a triangular prism P 23 (a second triangular prism), and the inclined surfaces of these prisms are mutually bonded. The optical member B1 and B2 are bonded so that the inclined surfaces of the diamond-shaped prism P12 and P22 are perpendicular from each other.

The trapezoidal prism P11 includes a top surface f11, an underside f12, inclined surface f13, vertical plane f14, and two planes which are parallel to the paper surface (not shown). When the length of the top surface f11 in the sheet surface is W, the length of the vertical plane f14 in the sheet surface is W, and the length of the underside f12 in the sheet surface is 2W. In addition, the angle (the angle with respect to the top surface f11 and the underside f12) of the inclined surface f13 is 45 degrees.

The diamond-shaped prism P12 includes the top surface f21 and the underside f22 which are parallel from each other, the inclined surface f23 and the inclined surface f24 which are parallel from each other, and two planes which are parallel to the sheet surface (not shown). Both the length of the top surface f21 and the underside f22 in the sheet surface are W, and the distance (height) between the top surface f21 and underside f22 is W. Moreover, the angle (the angle with respect to the top surface f21 and the underside f22) of the inclined surface f23 and the inclined surface f24 are 45 degrees. The triangular prism P13 includes an underside f31, a vertical plane f32, an inclined surface f33, and two planes which are parallel to the sheet surface (not shown). The length of the underside f31 and the vertical plane f32 in the sheet surface are W. Moreover, the angle (the angle with respect to the underside f31 and vertical planes f32) of the inclined surface f33 is 45 degrees.

The optical member B1 of which the shape of outside diameter is a quadrangular prism is formed by bonding the inclined surface f13 of the trapezoidal prism P11 to the inclined surface f23 of the diamond-shaped prism P12 together, and by bonding the inclined surface f24 of the diamond-shaped prism P12 to the inclined surface f33 of the triangular prism P13 together. Further, the surface of which the trapezoidal prism P1 and the diamond-shaped prism P12 are bonded is a translucent surface M1, and the surface of which the diamond-shaped prism P12 and the triangular prism P13 are bonded is a total reflection surface M2.

The trapezoidal prism P21 is composed of the same material as the trapezoidal prism P11. The trapezoidal prism P21 is the same shape as the trapezoidal prism P11. The diamond-shaped prism P22 is composed of the same material as the diamond-shaped prism P12. The diamond-shaped prism P22 is the same shape as the diamond-shaped prism P12. The triangular prism P23 is composed of the same material as the triangular prism P13. The triangular prism P23 is the same shape as the triangular prism P13. The optical member B2 of which the shape of the outside diameter is a quadrangular prism is formed by bonding the trapezoidal prism P21 to the diamond-shaped prism P22 and the triangular prism P23, in the same manner as the trapezoidal prism P11, the diamond-shaped prism P12, and the triangular prism P13. In addition, the surface which is bonding the trapezoidal prism P21 to the diamond-shaped prism P22 is a total reflection surface M3, and the surface which is bonding the diamond prism P22 to the triangular prism P23 is a total reflection surface M4.

The optical members B1 and B2 are formed by bonding perpendicularly the inclined surface f23 and the inclined surface f24 of the diamond-shaped prism P12. The optical path length of the split beam LB1 and the optical path length of the split beam LB2 in the beam splitter 21 are the same. In other words, the optical path length from the incident position Q1 of the reflected light L20 in the translucent surface M1 to the injection position Q11 (i.e., the position where the split beam LB1 is emitted from the beam splitter 21) of the reflected light L20 in the translucent surface M1, and the optical path length from the incident position Q1 of the reflected light L20 in the translucent surface M1 to the injection position Q12 (i.e., the position where the split beam LB2 is emitted from the beam splitter 21) of the reflected light L20 in the translucent surface M are same. The optical path length of the divided lights L21 to L24 are all same, in order to form plural divided lights L21 to L24 which are divided by the polarization divider 20 on the imaging surface 31a of the optical receiving element 31 provided in the optical receiver 30 (see FIG. 4: details will be described later).

Figure 4:
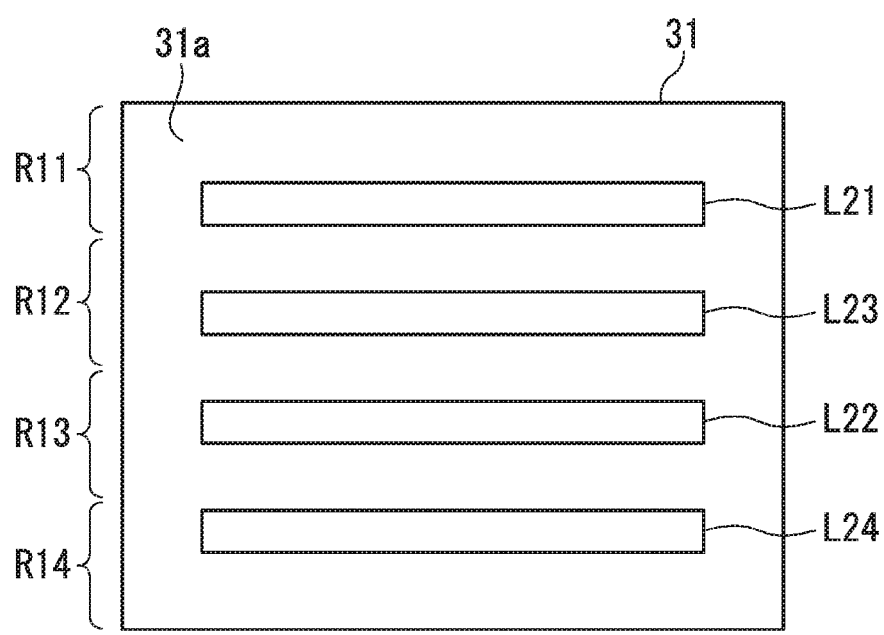
FIG. 4 is a diagram showing an image sensor element provided in an optical receiver according to the first embodiment of the present invention.

The optical receiver 30 is disposed on the surface side of the inspection target F as same as the polarization divider 20, and independently receives the plural divided lights L21 to L24 divided by the polarization divider 20. Specifically, the optical receiver 30, as shown in FIG. 4, for example, includes an optical receiving element 31 such as a CCD (Charge Coupled Device) or a CMOS (Complementary Metal Oxide Semiconductor). The optical receiver 30 independently obtains each of the plural divided lights L21 to L24 which are divided by the polarization divider 20 in mutually different areas of the imaging surface 31a of the image sensor 31. FIG. 4 is a diagram showing an image sensor element provided in an optical receiver according to the first embodiment of the present invention.

In the example shown in FIG. 4, the divided light L21 divided by the polarization divider 20 is imaged in the area R11 of the imaging surface 31a. The divided light L23 divided by the polarization divider 20 is imaged in the area R12 of the imaging surface 31a. The divided light L22 divided by the polarization divider 20 is imaged in the area R13 of the imaging surface 31a. The divided light L24 divided by the polarization divider 20 is imaged in the area R14 of the imaging surface 31a. The shape of the divided lights L21 to L24 being irradiated onto the imaging surface 31a of the optical receiving element 31 is generally similar to the shape of the inspection area R1 which is set on the inspection target F. Then, the optical receiver 30 outputs an image signal G which is imaged by the optical receiving element 31.

The processor 40 obtains an elliptical azimuth angle, a polarization degree, and a polarization component intensity by using the image signal G which is output from the optical receiver 30. The processor 40 determines the quality of the inspection target F. More specifically, the processor 40 processes the image signal G. The signal processing includes a processing of obtaining a luminance data I1 to I4 representing a luminance for each pixel (pixel of the optical receiving element 31), a processing of obtaining a stokes parameter S (S0 to S2) for each pixel from the luminance data I1 to I4, and a processing of obtaining an elliptical azimuth angle Ψ, a polarization degree DoP, and a polarization component intensity IP for each pixel using the stokes parameter S (S0 to S2). In other words, the processor 40 obtains a two-dimensional distribution of the elliptical azimuth angle Ψ, the polarization degree DoP, and the polarization component intensity IP in the inspection area R1 set on the inspection target F.

Here, the above-noted luminance data I1 represents the luminance of each pixel of the linearly polarized light L21 of which the vibration direction of the electric field is 0 degree, and the above-noted luminance data I2 represents the luminance of each pixel of the linearly polarized light L22 of which the vibration direction of the electric field is 45 degrees. The above-noted luminance data I3 represents the luminance of each pixel of the linearly polarized light L23 of which the vibration direction of the electric field is 90 degrees, and the above-noted luminance data I4 represents the luminance of each pixel of the linearly polarized light L24 of which the vibration direction of the electric field is 135 degrees.

The processor 40 obtains the stokes parameter S (S0 to S2) for each pixel by using the following formula (1). The processor 40 obtains the polarization degree DoP for each pixel by using the following formula (2). The processor 40 obtains the elliptical azimuth angle Ψ for each pixel by using the following formula (3). The processor 40 obtains the polarization component intensity IP for each pixel by using the following formula (4).

[formula 1]

$$S = \begin{pmatrix} S0 \\ S1 \\ S2 \end{pmatrix} = \begin{pmatrix} I1 + I3 \\ I1 - I3 \\ I2 - I4 \end{pmatrix} \quad (1)$$

[formula 2]

$$DoP = \frac{2 \cdot \sqrt{S1^2 + S2^2}}{I1 + I2 + I3 + I4} \quad (2)$$

[formula 3]

$$\Psi = \frac{1}{2} \tan^{-1}(S2/S1) \quad (3)$$

[formula 4]

$$IP = \frac{I1 + I2 + I3 + I4}{4} + \frac{\sqrt{S1^2 + S2^2}}{2} \cdot \cos(2(\theta - \Psi)) \quad (4)$$

The processor 40 includes an elliptical azimuth angle threshold TH1, a polarization degree threshold TH2, and a polarization component intensity threshold TH 3. The elliptical azimuth angle threshold TH1 is set to the elliptical azimuth angle Ψ. The elliptical azimuth angle Ψ is obtained by using the above-noted formula (3) in order to determine the quality of the inspection target F. The polarization degree threshold TH2 is set to the polarization degree DoP. The polarization degree DoP is obtained by using the formula (2) in order to determine the quality of the inspection target F. The polarization component intensity threshold TH3 is set to the polarization component intensity IP. The polarization component intensity IP is obtained by using the formula (4) in order to determine the quality of the inspection target F.

If the elliptical azimuth angle Ψ obtained by using formula (3) exceeds the elliptical azimuth angle threshold TH1, if the polarization degree DoP obtained by using the formula (2) exceeds the polarization component intensity threshold TH2, and if the polarization component intensity IP obtained by using the formula (4) exceeds the polarization component intensity threshold TH3, the processor 40 determines that the inspection target F is defective. If any one of (or any two of) the elliptical azimuth angle Ψ, the polarization degree DoP, and the polarization component intensity IP obtained by using the above formulae (3), (2), (4) exceeds the threshold, the processor 40 may determines the inspection target F is defective.

Next, the performance of the polarization inspector 1 in the above construction will be described. When the inspection started, the irradiator 10 is controlled by a controller (not shown), and the light source 11 emits the light of which the wavelength and the polarization condition is already known. The light emitted from the light source 11 makes incident on the polarizer 12, and the light is converted into the linearly polarized beam of light of which the vibration direction of the electric field is a direction which is perpendicular to the paper surface, and then the light makes incident on the ¼ wave plate 13, and is converted into the circularly polarized beam of light. Then, the light being converted into the circularly polarized beam of light (illumination light L10) is emitted from the irradiator 10 to irradiate the inspection area R1 which is set on the inspection target F.

If the illumination light L10 irradiates the inspection area R1 which is set on the inspection target F, the reflected light L20 of which the polarization condition changed is obtained. It should be noted that how the polarization condition of the reflected light L20 changes depends on the optical characteristics, the structure, and the film quality. The reflected light L20 reflected by the inspection area R1 which is set on the inspection target F makes incident on the polarization divider 20, and is spatially divided into plural divided lights L21 to L24 of which the direction of the polarizations are mutually different.

More specifically, if the reflected light L20 makes incident on the polarization divider 20, and then the reflected light L20 is split into the split beam LB1 and the split beam LB2 which are mutually parallel by the beam splitter 21 provided in the polarization divider 20 (refer to FIG. 2). As is shown in FIG. 3 in detail, the reflected light L20 makes incident on the diamond-shaped prism P12 which is one construction of the beam splitter 21, and the reflected light L20 is split into the transmitted light (the split beam LB1) and the reflected light (the split beam LB2) at the incident position Q1.

The split beam LB1 transmitted through the translucent surface M1 sequentially proceeds the trapezoidal prism P11 and the diamond-shaped prism P22, and is reflected by the total reflection surface M3. Further, the split beam LB1 proceeds in the diamond-shaped prism P22, and is reflected by the total reflection surface M4. Furthermore, the split beam LB1 proceeds in the diamond-shaped prism P22, and is injected from the injection position Q11 to the outside of the beam splitter 21. In contrast, the split beam LB2 reflected by the translucent surface M1 proceeds in the diamond-shaped prism P12. The split beam LB2 is reflected by the total reflection surface M2. The split beam LB2 sequentially proceeds in the diamond-shaped prism P 12 and the trapezoidal prism P21. The split beam LB2 is injected from the injection position Q12 to the outside of the beam splitter 21. In this way, the reflected light L20 is split into the split beam LB1 and the split beam LB2 which are mutually parallel.

The split beam LB1 being split by the beam splitter 21 makes incident on the polarization dividing element 23 as shown in FIG. 2. The split beam LB1 divides into the linearly polarized light L21 of which the vibration direction of the electric field is 0 degree and the linearly polarized light L23 of which the vibration direction of the electric field is 90 degrees. In contrast, as shown in FIG. 2, the split beam LB2 being split by the beam splitter 21 makes incident on the half-wavelength plate 22. The polarization direction of the split beam LB2 is rotated by 45 degrees. Further, the split beam LB2 makes incident on the polarization dividing element 23. The split beam LB2 is divided into the linearly polarized light L22 of which the vibration direction of the electric field is 45 degrees and the linearly polarized light L24 of which the vibration direction of the electric field is 135 degrees.

The optical receiver 30 independently receives the plural divided lights L21 to L24 which are spatially divided by the polarization divider 20. Specifically, as shown in FIG. 4, the plural divided lights L21 to L24 are independently imaged in mutually different areas on the imaging surface 31a of the optical receiving element 31 provided in the optical receiver 30. Then, the optical receiver 30 outputs an image signal G to the processor 40.

If the image signal G is input, the processor 40 firstly processes the image signal C, and obtains the luminance data I1 to I4 representing the luminance respectively for each pixel (the pixel of the optical receiving element 31). Then the processor 40 obtains stokes parameter S (S0 to S2) for each pixel from the luminance data I1 to I4 The processor 40 obtains the elliptical azimuth angle $\Psi$, the polarization degree DoP, and the polarization component intensity IP for each pixel by using the stokes parameter S (S0 to S2). Further, the processor 40 respectively compares the elliptical azimuth angle $\Psi$, the polarization degree DoP, and the polarization component intensity IP to the elliptical azimuth angle threshold TH1, the polarization degree threshold TH2, and the polarization component intensity threshold TH3 in every luminance data I1 to I4, and then determines the quality of the inspection target F.

For example, If the elliptical azimuth angle $\Psi$ exceeds the elliptical azimuth angle threshold TH1, if the polarization degree DoP exceeds the polarization component intensity threshold TH2, and if the polarization component intensity IP exceeds the polarization component intensity threshold TH3, the processor 40 determines that the inspection target F is defective. In contrast, any one of the elliptical azimuth angle $\Psi$, the polarization degree DoP, and the polarization component intensity IP does not exceed the threshold, the processor 40 may determine that the inspection target F is good (non-defective).

The processor 40 is, for example, displays the determination result described above on a display (not shown) provided in the processor 40, and notifies by using sound or the like, or transmits to a host device (not shown). By repeating the process described above in a condition which the inspection target F is transporting in the transport direction X, the quality of the inspection target F in the conveying direction X is continuously inspected in the width of the inspection area R1 in the width direction Y.

As described above, the illumination light L10 of which a polarization condition is already known is irradiated onto the inspection area R1 of the inspection target F, the reflected light L20 obtained from the inspection target F is spatially divided into the plural divided lights L21 to L24 which the polarization directions are mutually different. Then, the divided lights L21 to L24 is independently received, and the elliptical azimuth angle $\Psi$, the polarization degree DoP, and the polarization component intensity IP is obtained by using the detected image signal G. Further, the quality of the inspection target F is determined.

Therefore, it is possible to simultaneously measure the plural divided lights L21 to L24 of which the polarization directions are mutually different. Since an efficiency of the reflected light L20 is also good, it can be performed to inspect the inspection target F in a short time. Thus, even when the inspection target F is transporting, it is possible to accurately inspect the film quality of the inspection target F. Further, since it is not necessary to rotate the analyzer such as the case of inspection by using the rotating analyzer in the present embodiment, it can miniaturize the device, and it can inspect the inspection target at a lower cost. Since the images on the inspection area R1 of the rectangular shape which is set on the inspection target F is captured by the optical receiving element 31 in the present embodiment, it is possible to inspect the film quality of the inspection target F even if the inspection target F is not transporting.

<Second Embodiment>

Figure 5:
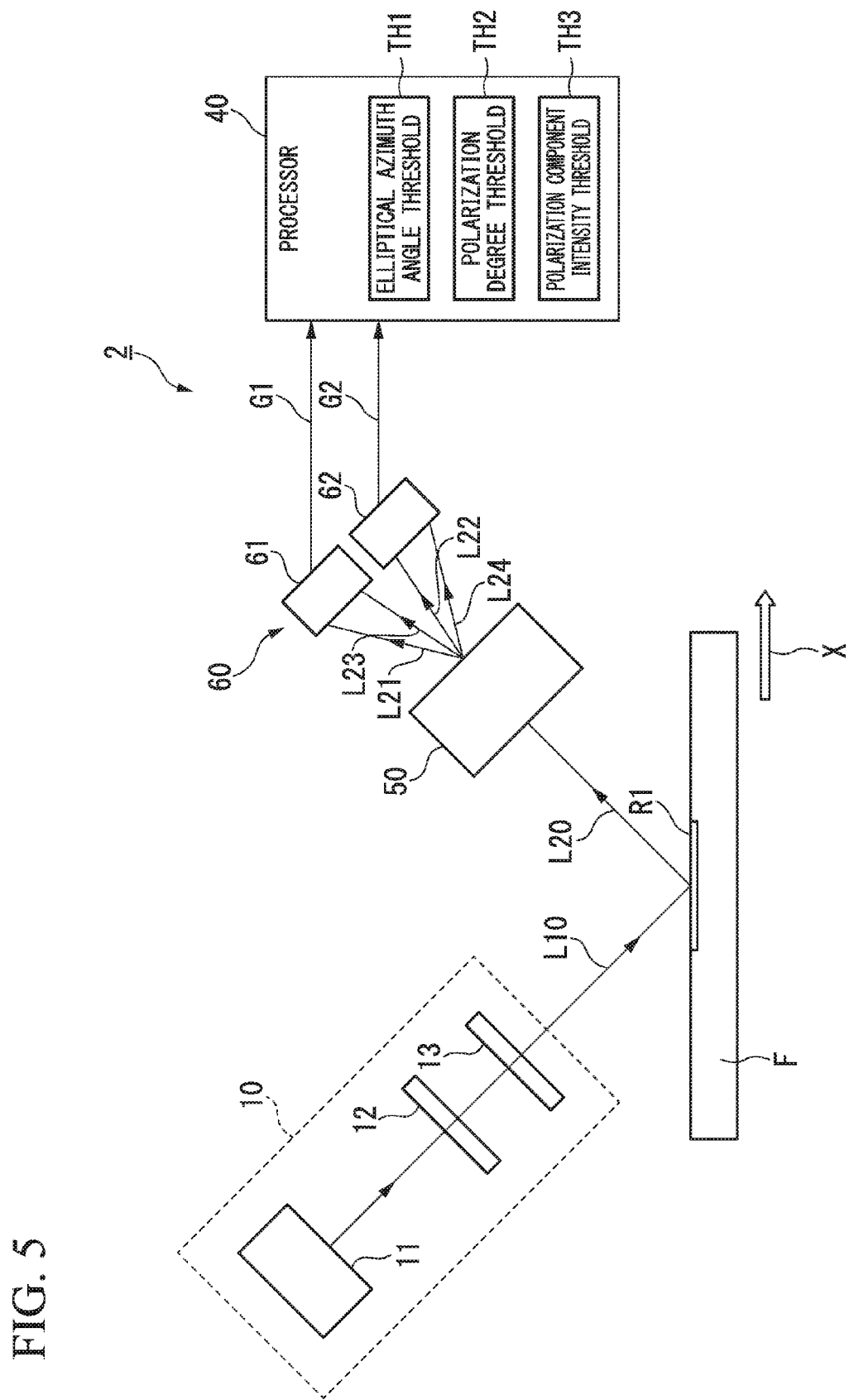
FIG. 5 is a block diagram showing a main construction of the polarization inspector according to a second embodiment of the present invention.

FIG. 5 is a block diagram showing a main construction of a polarization inspector according to a second embodiment of the present invention. Incidentally, the devices or units or components in FIG. 5 corresponding to the devices or units or components shown in FIG. 1 are assigned to the same reference numerals as FIG. 1. In a construction of a polarization inspector 2 shown in FIG. 5, the polarization divider 20 and the optical receiver 30 provided in the polarization inspector 1 shown in FIG. 1 is respectively changed to a polarization divider (dividor) 50 and an optical receiver 60.

The polarization divider 50 is, similarly to the polarization divider 20 shown in FIG. 1, disposed on the surface side of the inspection target F. The polarization divider 50 spatially divides the reflected light L20 obtained from the inspection target F into the plural divided lights L21 to L24 of which the polarization directions are mutually different. However, the specific construction of the polarization divider 50 is different from the construction of the polarization divider 20. The optical receiver 60, similarly to the optical receiver 30 shown in FIG. 1, are disposed on the surface side of the inspection target F. The optical receiver 60 independently receives the plural divided lights L21 to L24 divided by the polarization divider 50. However, the specific construction of the optical receiver 60 is different from the construction of the optical receiver 30.

Figure 6:
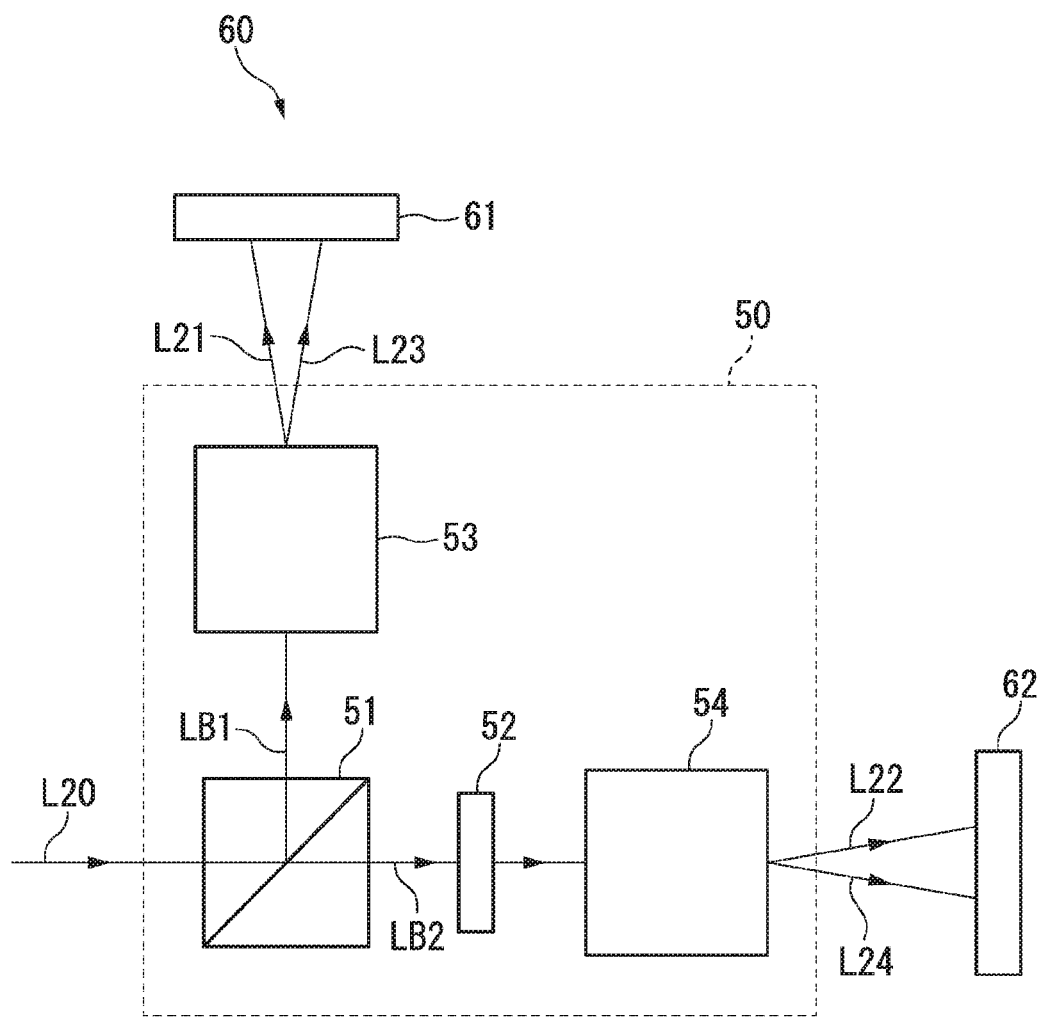
FIG. 6 is a block diagram showing a construction of a polarization divider and an optical receiver provided in the polarization inspector according to the second embodiment of the present invention.

FIG. 6 is a block diagram showing a construction of a polarization divider and an optical receiver provided in the polarization inspector according to the second embodiment of the present invention. As shown in FIG. 6, the polarization divider 50 includes a beam splitter 51, a half-wavelength plate 52 (a second divider, a wavelength plate, a wavelength device), a polarization dividing element 53 (a first divider), and a polarization dividing element 54 (a second divider).

The beam splitter 51 splits the reflected light L20 obtained from the inspection target F into the split beam LB1 (a first split beam) and the split beam LB2 (a second split beam) which proceeds to the mutually different directions. The beam splitter 51 may be, for example, a half mirror or a beam splitter. The beam splitter 51 splits the reflected light L20 obtained from the inspection target F into the reflected light (the split beam LB1) and the transmitted light (the split beam LB2). The half-wavelength plate 22 is disposed on the optical path of the split beam LB2, and rotates by 45 degrees the polarization direction of the split beam LB2. Incidentally, the half-wavelength plate 22 may be disposed on the optical path of the split beam LB1.

The polarization dividing element 53, for example, includes a Wollaston Prism. The polarization dividing element 53 is disposed on the optical path of the split beam LB1. The polarization dividing element 53 divides the split beam LB1 into plural divided lights of which the polarization directions are mutually perpendicular. Specifically, the polarization dividing element 53 divides the split beam LB1 into the linearly polarized light L21 of which the vibration direction of the electric field is 0 degree and the linearly polarized light L23 of which the vibration direction of the electric field is 90 degrees. The polarization dividing element 54 includes, for example, the Wollaston Prism which is similar to the polarization dividing element 53. The polarization dividing element 54 disposed on the optical path of the split beam LB2 transmitted through the half-wavelength plate 52. The polarization dividing element 54 divides the split beam LB2 transmitted through the half-wavelength plate 52 into plural divided lights of which the polarization directions are mutually perpendicular. Specifically, the polarization dividing element 54 divides the split beam LB2 transmitted through the half-wavelength plate 52 into the linearly polarized light L22 of which the vibration direction of the electric field is 45 degrees and the linearly polarized light L24 of which the vibration direction of the electric field is 135 degrees.

The optical receiver 60, as shown in FIG. 6, includes an optical receiving element 61 (a first optical receiving element) and an optical receiving element 62 (a second optical receiving element). The optical receiving element 61 and the optical receiving elements 62 may be, for example, a CCD or CMOS as same as the optical receiving element 31 shown in FIG. 4. The optical receiving element 61 is independently obtains the respective divided lights L21 and L23 divided by the polarization divider 50 in the mutually different areas of the imaging surface 61a. The optical receiving element 62 is independently captures the respective divided lights L22 and L24 divided by the polarization divider 50 in the mutually different areas of the imaging surface 62a.

Figure 7:
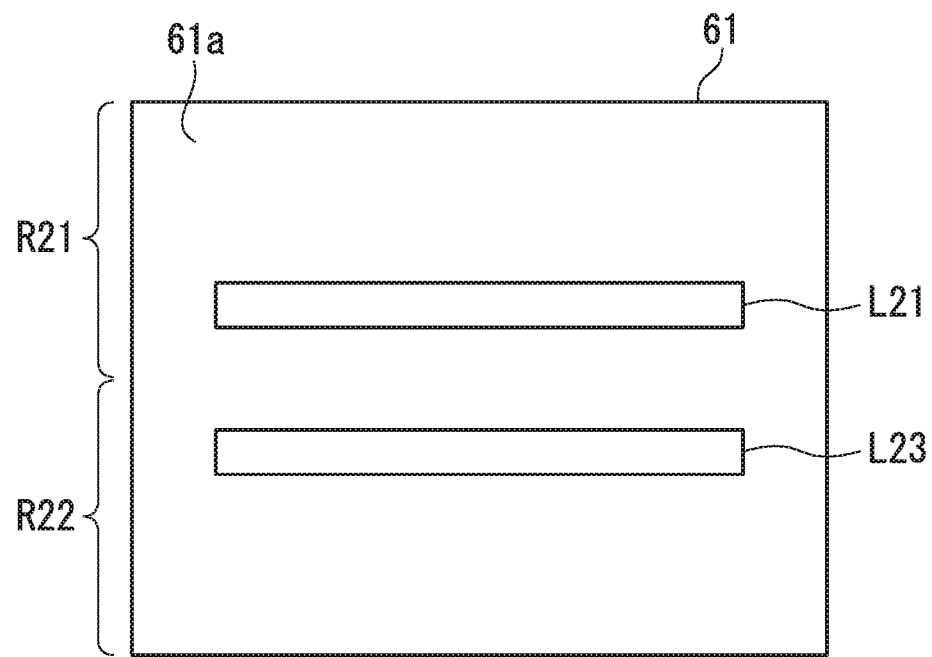
FIG. 7 is a diagram showing an image sensor element provided in the optical receiver according to the second embodiment of the present invention.
Figure 7:
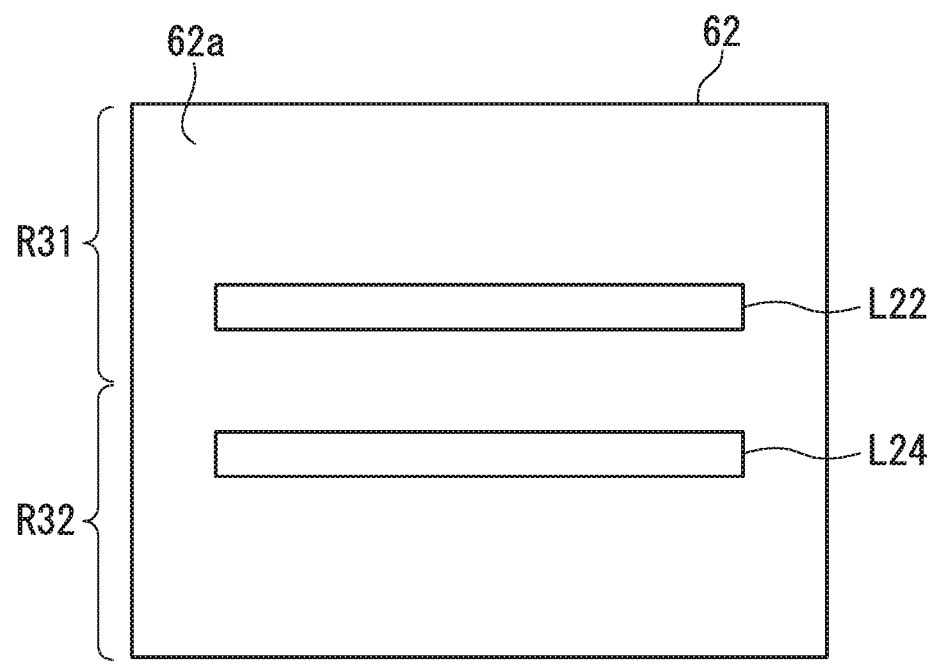

FIG. 7 is a diagram showing an image sensor element provided in an optical receiver according to the second embodiment of the present invention. Note that FIG. 7 illustrates the optical receiving element 61 and 62 so that the imaging surface 61a and 62a face forward. In the example shown in FIG. 7, the divided light L21 which is divided by the polarization divider 50 is captured in the area R21 which constructs the imaging surface 61a provided in the optical receiving element 61. The divided light L22 which is divided by the polarization divider 50 is captured in the area R22 which constructs the imaging surface 61a provided in the optical receiving element 61. Further, the divided light L22 divided by the polarization divider 50 is captured in the area R31 which constructs the imaging surface 62a provided in the optical receiving element 62. The divided light L24 divided by the polarization divider 50 is captured in the area R32 which constructs the imaging surface 62 provided in the optical receiving element 62.

The shape of the divided lights L22 and L24 which irradiates the imaging surface 61a provided on the optical receiving element 61 generally similar to the shape of the inspection area R1 which is set on the inspection target F such as the first embodiment. The shape of the divided lights L22 and L24 which irradiates the imaging surface 62a provided on the optical receiving element 62 generally similar to the shape of the inspection area R1 which is set on the inspection target F such as the first embodiment. The optical receiver 60, as shown in FIG. 5, outputs the image signals G1 captured by the optical receiving element 61, and the image signal G2 captured by the optical receiving element 62.

Next, the behavior of the polarization inspector 2 in the above construction will be described. Since the behavior of the polarization inspector 2 is basically the same as the polarization inspector 1 shown in FIG. 1, the following description will be simplified. When the inspection starts, the controller (not shown) controls the irradiator 10, and the light source 11 emits the light of which the wavelength and polarization condition is already known. The light emitted from the light source 11 sequentially transmits through the polarizer 12 and the quarter-wave plate 13, thereby which is converted to the linearly polarized beam of light, and then which is converted into the circularly polarized beam of light. Then, the light (the illumination light L10) which is converted into the circularly polarized beam of light is emitted from the irradiator 10. The illumination light L10 irradiates the inspection area R1 which is set on the inspection target F.

If the illumination light L10 irradiates the inspection area R1 which is set on the inspection target F, the reflected light L20 of which the polarization condition changed is obtained. The reflected light L20 which is reflected by the inspection area R1 which is set on the inspection target F is incident on the polarization divider 50. The polarization divider 50 spatially divides the reflected light L20 into the plural divided lights L21 to L24 of which the polarization directions are mutually different. More specifically, if the reflected light L20 is incident on the polarization divider 50, firstly the beam splitter 51 provided in the polarization divider 50 splits the reflected light L20 into the reflected light (the split beam LB1) and the transmitted light (the split beam LB2).

The split beam LB1 which is split by the beam splitter 51 is incident on the polarization dividing element 53 as shown in FIG. 6. Then the split beam LB1 is divided into the linearly polarized light L21 of which the vibration direction of the electric field is 0 degree and the linearly polarized light L23 of which the vibration direction of the electric field is 90 degrees. In contrast, as shown in FIG. 6, the split beam LB2 which is split by the beam splitter 51 is incident on the half-wavelength plate 52, and rotates by 45 degrees the polarization direction. Further, the split beam LB2 is incident on the polarization dividing element 53. Furthermore, the split beam LB2 is divided into the linearly polarized light L22 of which the vibration direction of the electric field is 45 degrees and the linearly polarized light L24 of which the vibration direction of the electric field is 135 degrees.

The optical receiver 60 independently receives the plural divided lights L21 to L24 which are spatially divided by the polarization divider 50. Specifically, as shown in FIG. 7, the divided lights L21 and L23 among the plural divided lights L21 to L24 are independently captured in the mutually different areas on the imaging surface 61a which is provided in the optical receiving element 61 of the optical receiver 60. Then, the other divided lights L22 and L24 are independently imaged in the mutually different areas on the imaging surface 62a provided in the optical receiving element 62 of the optical receiver 60. Further, when the optical receiving element 62 captures images the plural divided lights L21 to L24 which are spatially divided by the polarization divider 50, the optical receiver 60 outputs the image signals G1 and G2 to the processor 40.

If the image signal G1 and G2 are input to the processor 40 from the optical receiver 60, the processor 40, similarly to the first embodiment, sequentially obtains the stokes parameter S (S0 to S2) for each pixel from the luminance data I1 to I4. Then, the processor 40 obtains the elliptical azimuth angle Ψ, the polarization degree DoP, and the polarization component intensity IP for each pixel by using the stokes parameter S (S0 to S2). Further, the processor 40 respectively compares the elliptical azimuth angle Ψ, the polarization degree DoP and the polarization component intensity IP with the elliptical azimuth angle threshold TH1, the polarization degree threshold TH2 and the polarization component intensity threshold TH 3, and then the processor 40 determines the quality of the inspection target F. The above mentioned processing is repeated in the condition where the inspection target F is transporting in the transport direction X, the film quality of the inspection target F in the conveying direction X is continuously inspected in the width of the inspection area R2 in the width direction Y.

Figure 8:
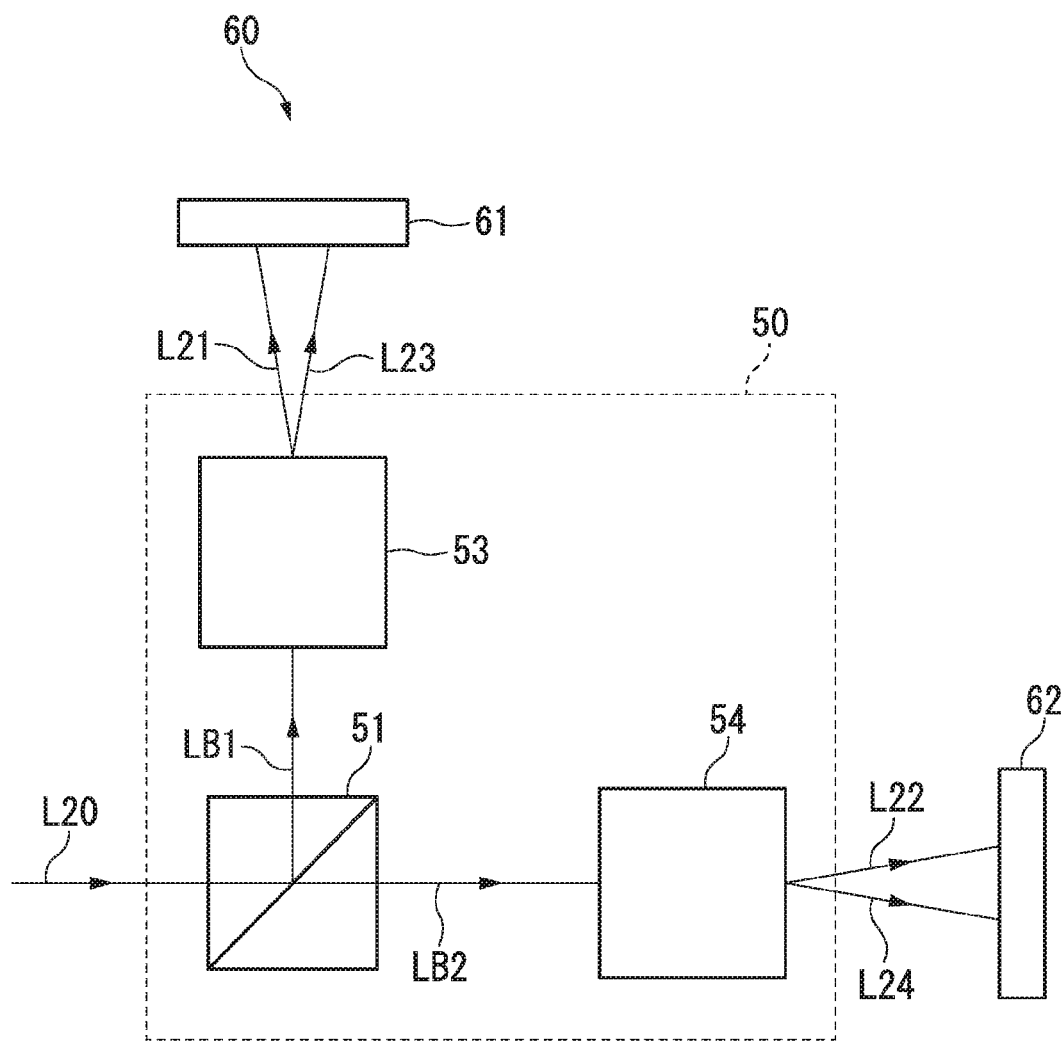
FIG. 8 is a block diagram showing a modified example of the polarization divider provided on the polarization inspector according to the second embodiment of the present invention.

FIG. 8 is a block diagram showing a modified example of the polarization divider provided in the polarization inspector according to the second embodiment of the present invention. Incidentally, the constructions in FIG. 8 corresponding to the construction shown in FIG. 6 are assigned to the same reference numerals as FIG. 6. As shown in FIG. 8, the polarization divider 50 according to the present embodiment omits the half-wavelength plate 52 from the polarization divider 50 shown in FIG. 6. The arrangement of the polarization dividing element 54 in the polarization divider 50 is modified. Specifically, the polarization dividing element 54 is arranged in a condition of which the progressing direction of the split beam LB2 is rotated by 45 degrees. That is, when the polarization dividing element 53, 54 are viewed from the optical axis direction, the one is arranged so that the other forms an angle 45 degrees to the one (such as the crystal optical axis forms an angle of 45 degrees).

The polarization divider 50 according to the present modified embodiment similarly to the polarization divider 50 shown in FIG. 6 can spatially divide the reflected light L20 obtained from the inspection target F into the plural divided lights L21 to L24 of which polarization directions are mutually different. Incidentally, the polarization divider 50 according to the present modified example can omit the half-wavelength plate 52 as compared with the polarization divider 50 shown in FIG. 6. The polarization divider 50 according to the present modified example can reduce the cost by reducing the number of component parts. Further, the cost required for the component adjusting can be reduced.

As described above, in the present embodiment and the present modified embodiment, the illumination light L10 of which the polarization condition is already known irradiates the inspection area R1 of the inspection target F as same as in the first embodiment. The polarization divider 50 spatially divides the reflected light L20 obtained from the inspection target F into the plural divided lights L21 to L24 of which the polarized direction are mutually different. Then, the optical receiver 60 independently receives the divided lights L21 to L24. The processor 40 obtains the image signals G1 and G2 from the divided lights L21 to L24. The processor 40 obtains the elliptical azimuth angle Ψ, the polarization degree DoP, and the polarization component intensity IP by using the image signals G1 and G2. Then, the processor 40 determines the quality of the inspection target F. Therefore, it is possible to inspect the film quality of inspection target F accurately, at a low cost by the small device regardless of whether or not the inspection target F is in the moving condition.

<Third Embodiment>

Figure 9:
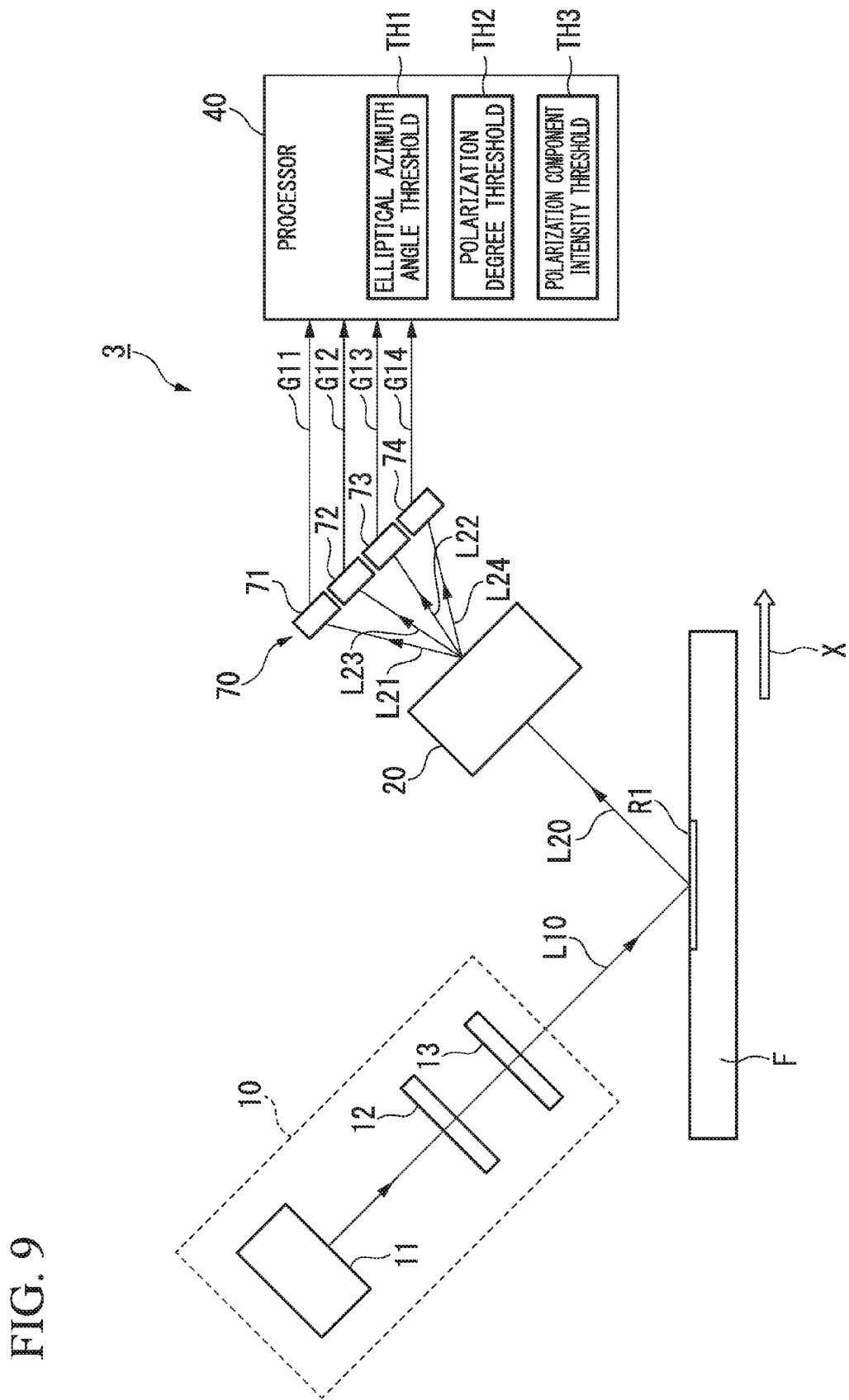
FIG. 9 is a block diagram showing a main construction of a polarization inspector according to a third embodiment of the present invention.

FIG. 9 is a block diagram showing a main construction of a polarization inspector according to a third embodiment of the present invention. Incidentally, the constructions shown in FIG. 9 which are corresponding to the construction shown in FIG. 1 are assigned to the same reference numerals as FIG. 1. The optical receiver 70 provided in the polarization inspector 3 shown in FIG. 9 is corresponding to the optical receiver 30 provided in the polarization inspector 1 shown in FIG. 1.

The optical receiver 70 includes a plural optical receiving elements which are provided in correspondence with each of the plural divided lights L21 to L24 which are divided by the polarization divider 20. Specifically, the optical receiver 70 includes an optical receiving element 71 which is provided in correspondence with the divided light L21, an optical receiving element 72 which is provided in correspondence with the divided light L23, an optical receiving element 73 which is provided in correspondence with the divided light L22, and an optical receiving element 74 which is provided in correspondence with the divided light L24. These optical receiving elements 71 to 74 may be, for example, a one-dimensional optical receiving element (a line sensor).

The optical receiving elements 71, 72, 73, and 74 are respectively arranged on the optical path of the divided lights L21, L23, L22, and L24, along with the longitudinal direction of the divided lights L21, L23, L22, and L24. Plural divided lights L21 L23, L22, and L24 which are spatially divided by the polarization divider 20 are respectively captured by the optical receiving elements 71, 72, 73, and 74. Then, the image signals G11, G12, G13, and G14 (a one-dimensional image signal) are output respectively from the optical receiver 70 to the processor 40. The similar processing with the first embodiment and the second embodiment is performed to the image signals G11, G12, G13, and G14. Thereby, the film quality of the inspection target F in the conveying direction X is continuously inspected in the width of the inspection area R1 in the width direction Y. Incidentally, the description thereof is omitted since the operation of the polarization inspector 3 is basically similar to the polarization inspector 1 and 2.

As described above, in the present embodiment same as in the first embodiment, the illumination light L10 of which the polarization condition is already known irradiates the inspection area R1 of the inspection target F. The polarization divider 50 spatially divides the reflected light L20 obtained from the inspection target F into plural divided lights L21 to L24 of which the polarized direction are mutually different. Then, the optical receiver 70 independently receives the divided lights L21 to L24, and the processor 40 obtains the image signals G11, G12, G13, and G14. The processor 40 obtains the elliptical azimuth angle Ψ, the polarization degree DoP, and the polarization component intensity IP by using the image signals G11, G12, G13, and G14. Thereby, the processor 40 determines the quality of the inspection target F. Therefore, although the number of the optical receiving element is increased than the first embodiment, regardless of whether or not the inspection target F is in the condition of moving, it is possible to accurately inspect the film quality of inspection target F at a low cost by the small device.

Incidentally, it is possible to apply the optical receiver 70 of the present embodiment to the second embodiment. That is, the optical receiver 70 provided in the polarization inspector 3 described above is corresponding to the optical receiver 30 provided in the polarization inspector 1 shown in FIG. 1. Further, the optical receiver 60 in the polarization inspector 2 shown in FIG. 5 may also be changed to the optical receiver 70.

Figure 10:
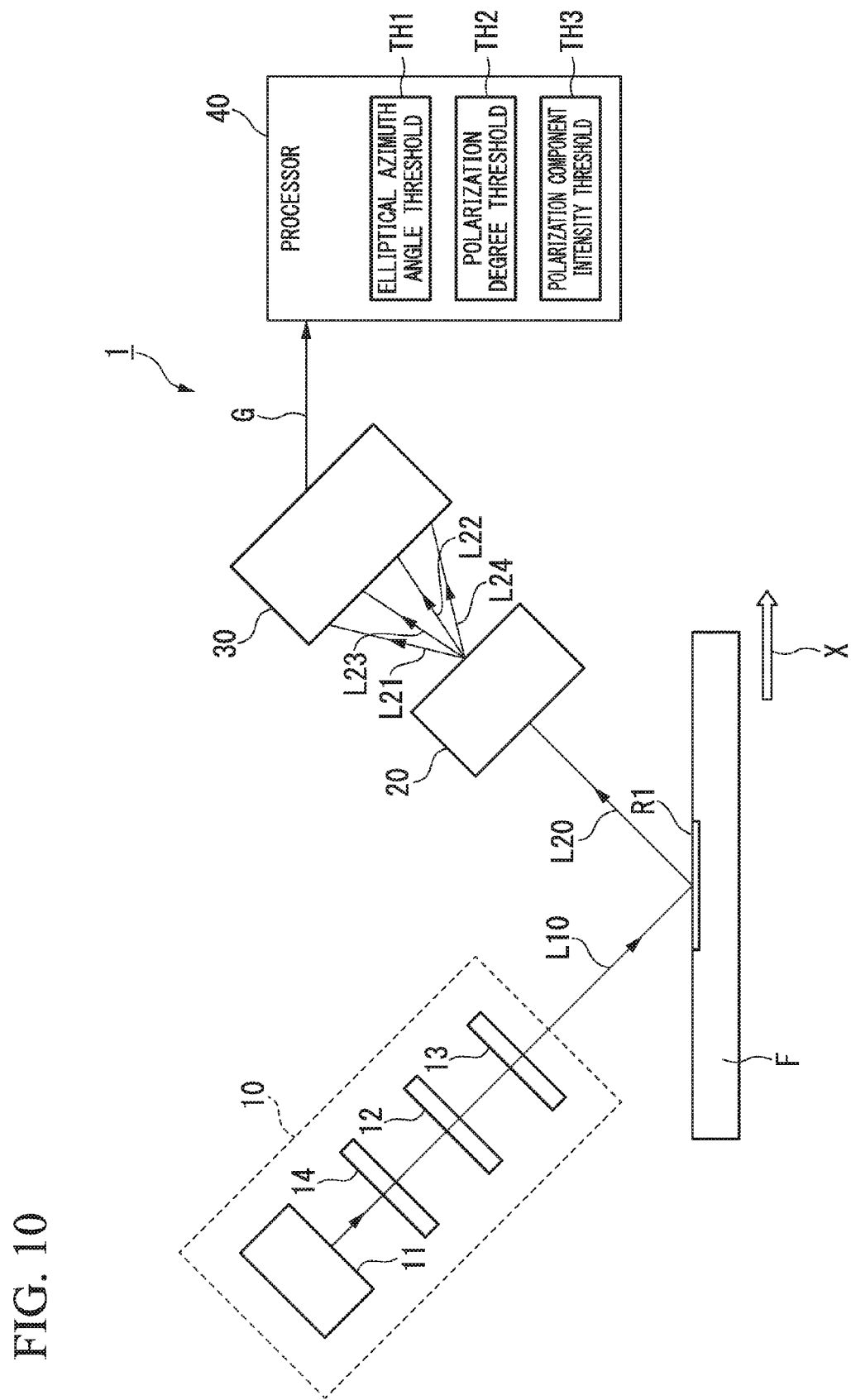
FIG. 10 is a diagram showing a construction of the polarization inspector providing a wavelength filter in an irradiator.

The polarization inspector according to the embodiment of the present invention has been described above, the present invention is not limited to the above embodiments and can be freely modified within the scope of the present invention. For example, the irradiator 10 described in the first to third embodiment includes the light source 11, the polarizer 12, and a quarter-wave plate 13, and the irradiator 10 may further includes a wavelength filter in addition to the above-noted devices. FIG. 10 is a diagram showing a construction of a polarization inspector of which a wavelength filter is provided in the irradiator. FIG. 10 illustrates an example of the polarization inspector 1 of the first embodiment. Further, it is possible to provide the wavelength filter in the irradiator 10 of the polarization inspector 2 and 3 of the second and third embodiment as same as the polarization inspector 1 of the first embodiment.

The wavelength filter 14 which is provided in the irradiator 10 includes characteristics that passes only light having a predefined wavelength or light of a predefined wavelength band. For example, the wavelength filter 14 is intended to include a characteristic of excluding (not passing) the wavelength components which deteriorates the inspection accuracy of the inspection target F among the wavelength components contained in the illuminating light L10. According to use such a wavelength filter 14, it is possible to prevent deterioration of the inspection accuracy of the inspection target F.

Further, in the above-described embodiment, the processor 40 obtains the elliptical azimuth angle Ψ, the polarization degree DoP, and the polarization component intensity IP, and thereby determines the quality of the inspection target F. It is not necessary to obtain the elliptical azimuth angle Ψ, the polarization degree DoP, and the polarization component intensity IP. It may be subjected to obtain any one (or any two) of the elliptical azimuth angle Ψ, the polarization degree DoP, and the polarization component intensity IP to determine the quality of the inspection target F.

Furthermore, in the above embodiment, the example of the case has been explained that the processor 40 obtains the two-dimensional distribution of the elliptical azimuth angle Ψ, the polarization degree DoP, and the polarization component intensity IP on the inspection area R1 which is set on the inspection target F. It is not necessary to obtain the two-dimensional distribution of the elliptical azimuth angle Ψ, the polarization degree DoP, and the polarization component intensity IP. It may be subjected to obtain only the representative values of the elliptical azimuth angle Ψ, the polarization degree DoP, and the polarization component intensity IP to determine the quality of the inspection target F on the inspection area R1.

Figure 11:
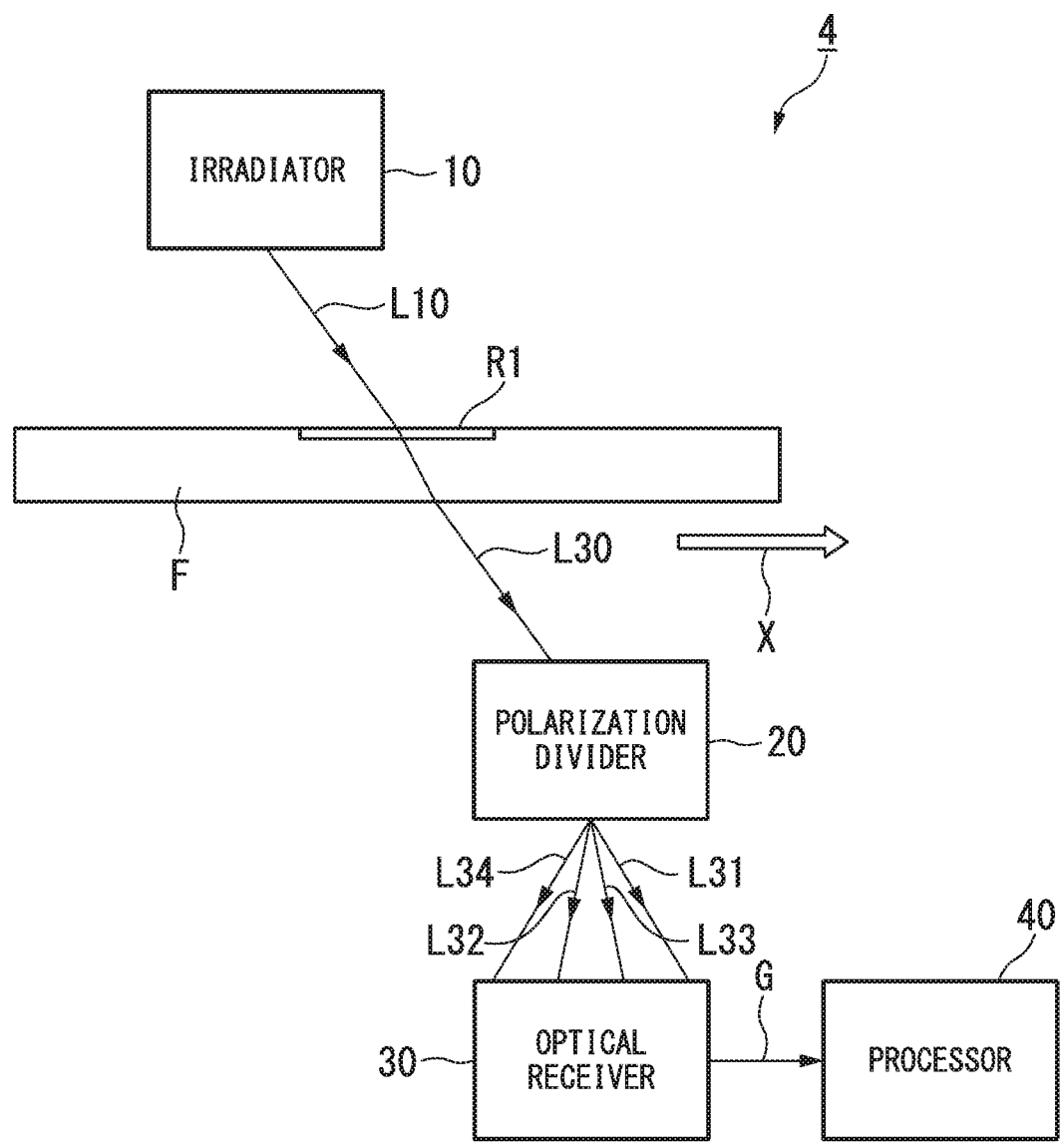
FIG. 11 is a block diagram showing a schematic construction of the polarization inspector in a transmission system.

Moreover, the polarization inspector 1 to 3 described in the first to third embodiments employ a reflective method for inspecting the filter quality of the inspection target F by receiving the reflected light L20 obtained from the inspection target F. The present invention can also be applied to the polarization inspector of a transmission method for inspecting the film quality of the inspection target F by using the transmitted light by receiving the transmitted light which is transmitted through the inspection target F. FIG. 11 is a block diagram showing a schematic construction of a polarization inspector in a transmission method. The polarization inspector 4 shown in FIG. 11 arranges the irradiator 10 on the surface side of the inspection target F, and arranges the polarization divider 20 and the optical receiver 30 on the back side of the inspection target F. The process unit 40 may be arranged in any of the surface side and the back side of the inspection target F.

The polarization inspector 4 irradiates the inspection area R1 which is set in the inspection target F with the illumination light L10 of which the polarization condition is already known. The polarization divider 20 spatially divides the transmitted light L30 obtained from the inspection target F into the plural lights L31 to L34 of which the polarization directions are mutually different. The optical receiver 30 independently receives the light L31 to L34. The processor 40 obtains the elliptical azimuth angle Ψ, the polarization degree DoP, and the polarization component intensity IP by using the image signal G obtained by the optical receiver 30. Thereby the processor 40 determines the film quality of the inspection target F.

Further, the present invention can also be applied to those which the polarization inspector of the reflection system and the polarization inspector of the transmission system as described above are combined. Such the polarization inspector, for example, arranges the irradiator 10 on the surface side of the inspection target F, and arranges the polarization divider 20 and the optical receiver 30 on both the surface side and the back side of the inspection target F.

What is claimed is:

1. A polarization inspector for inspecting an inspection target, the polarization inspector comprising:
   a polarization divider configured to spatially divide at least a reflected beam of light from the inspection target into divided beams of lights which are mutually different in polarization direction;
   one or more optical receivers configured to receive the divided beams of lights and to generate an image signal based on the divided beams of lights; and
   a processor configured to calculate at least one of an elliptical azimuth angle, a polarization degree and a polarization component intensity from the image signal,
   wherein
   the polarization divider comprises:
   a beam splitter configured to split at least the reflected beam of light having the polarization direction obtained from the inspection target into a first split beam of light and a second split beam of light;
   a wavelength device configured to rotate by 45 degrees either one of the first split beam of light or the second split beam of light to differentiate in polarization direction by 45 degrees between the first split beam of light and the second split beam of light; and
   a polarization dividing element configured to obtain the first split beam which was not transmitted through the wavelength device and the second split beam which was transmitted through the wavelength device, to divide each of the first split beam and the second split beam into plural divided lights of which the polarization directions are mutually perpendicular, and wherein
   the polarization dividing element comprises:
   a first optical member that comprises a first trapezoidal prism, a first diamond-shaped prism, and a first triangular prism are mutually bonded; and
   a second optical member that comprises a second trapezoidal prism, a second diamond-shaped prism, and a second triangular prism are mutually bonded; wherein
   the first optical member and the second optical member are bonded such that the surface of the first diamond-shaped prism of the first optical member and the surface of the second diamond-shaped prism of the second optical member are perpendicular.

2. The polarization inspector according to claim 1, wherein
   the surface of which the first trapezoidal prism and the first diamond-shaped prism are bonded is a translucent surface, and
   each the surface of which the first diamond-shaped prism and the first triangular prism of the first optical member are bonded, the surface of which the second trapezoidal prism and the second diamond-shaped prism of the second optical member are bonded, and the surface of which the second diamond-shaped prism and the second triangular prism of the second optical member are bonded is a total reflection surface.

3. The polarization inspector according to claim 2, wherein
   the optical receiver comprises an image sensor configured to independently obtain each of the plural divided beams of lights which are divided by the polarization divider in mutually different areas of an imaging surface.

4. The polarization inspector according to claim 1, wherein
   the optical receiver comprises an image sensor configured to independently obtain each of the plural divided beams of lights which are divided by the polarization divider in mutually different areas of an imaging surface.

5. The polarization inspector according to claim 1, wherein
   the optical receiver comprises an image sensor configured to independently obtain each of the plural divided beams of lights which are divided by the polarization divider in mutually different areas of an imaging surface.

6. The polarization inspector according to claim 1, wherein
   the optical receiver comprises an image sensor configured to independently obtain each of the plural divided beams of lights which are divided by the polarization divider in mutually different areas of an imaging surface.

7. The polarization inspector according to claim 1, wherein
   the polarization divider comprises:
   a beam splitter configured to split at least the reflected beam of light obtained from the inspection target into a first split beam of light and a second split beam of light which proceeds to the mutually different directions;
   a first divider configured to divide the first split beam of light into plural divided beams of lights of which the polarization directions are mutually perpendicular; and
   a second divider configured to divide the second split beam of light into plural divided beams of lights of which the polarization directions are mutually perpendicular and each of the polarization directions form 45 degrees to the polarization directions of the divided beams of lights divided by the first divider.

8. The polarization inspector according to claim 7, wherein
   the first divider comprises a polarization dividing element configured to divide the first split beam of light into the plural divided beams of lights of which the polarization directions are mutually perpendicular;
   the second divider comprises a wavelength device configured to rotate by 45 degrees the polarization direction of the second split beam of light and a polarization dividing element configured to divide the second split beam of light which transmitted through the wavelength device into the plural divided beams of lights of which the polarization directions are mutually perpendicular.

9. The polarization inspector according to claim 8, wherein
   the optical receiver comprises:
   a first optical receiving element configured to independently obtain the plural respective divided beams of lights divided by the first divider in the mutually different areas of the imaging surface; and
   a second optical receiving element configured to independently obtain the plural respective divided beams of lights divided by the second divider in the mutually different areas of the imaging surface.

10. The polarization inspector according to claim 7, wherein
the first divider comprises a first polarization dividing element configured to divide the first split beam of light into the plural divided beams of lights of which the polarization directions are mutually perpendicular;
the second divider comprises a second polarization dividing element configured to divide the second split beam of light into the plural divided beams of lights of which the polarization directions are mutually perpendicular;
the first polarization dividing element is configured to arrange that the first polarization dividing element forms 45 degrees to the crystal axis direction of the first split beam of light; and
the second polarization dividing element is configured to arrange that the second polarization dividing element forms 45 degrees to the crystal axis direction of the second split beam of light.

11. The polarization inspector according to claim 10, wherein
the optical receiver comprises:
a first optical receiving element configured to independently obtain the plural respective divided beams of lights divided by the first divider in the mutually different areas of the imaging surface; and
a second optical receiving element configured to independently obtain the plural respective divided beams of lights divided by the second divider in the mutually different areas of the imaging surface.

12. The polarization inspector according to claim 7, wherein
the optical receiver comprises:
a first optical receiving element configured to independently obtain the plural respective divided beams of lights divided by the first divider in the mutually different areas of the imaging surface; and
a second optical receiving element configured to independently obtain the plural respective divided beams of lights divided by the second divider in the mutually different areas of the imaging surface.

13. The polarization inspector according to claim 1, wherein
the optical receiver comprises optical receiving elements that are arranged in accordance with the plural respective divided beams of lights divided by the polarization divider.

14. The polarization inspector according to claim 1, wherein
the optical receiver comprises optical receiving elements that are arranged in accordance with the plural respective divided beams of lights divided by the polarization divider.

15. The polarization inspector according to claim 1, wherein
the optical receiver comprises optical receiving elements that are arranged in accordance with the plural respective divided beams of lights divided by the polarization divider.

16. The polarization inspector according to claim 1, further comprising:
an irradiator configured to irradiate an illumination beam of light to the inspection target; wherein
the irradiator comprises a wavelength filter configured to pass only a light having a predefined wavelength or a light of a predefined wavelength band.

17. The polarization inspector according to claims 1, wherein
the polarization divider is configured to spatially divide the reflected beam of light of which the illumination beam of light is reflected by the inspection target or the transmitted beam of light of which the illumination beam of light is transmitted through the inspection target into the plural divided beams of lights of which the polarization directions are mutually different.

18. A polarization divider configured to spatially divide at least a reflected beam of light from the inspection target into divided beams of lights which are mutually different in polarization direction, the polarization divider comprising:
a beam splitter configured to split at least the reflected beam of light having the polarization direction obtained from the inspection target into a first split beam of light and a second split beam of light;
a wavelength device configured to rotate by 45 degrees either one of the first split beam of light or the second split beam of light to differentiate in polarization direction by 45 degrees between the first split beam of light and the second split beam of light; and
a polarization dividing element configured to obtain the first split beam which was not transmitted through the wavelength device and the second split beam which was transmitted through the wavelength device, to divide each of the first split beam and the second split beam into plural divided lights of which the polarization directions are mutually perpendicular,
wherein
the polarization dividing element comprises:
a first optical member that comprises a first trapezoidal prism, a first diamond-shaped prism, and a first triangular prism are mutually bonded; and
a second optical member that comprises a second trapezoidal prism, a second diamond-shaped prism, and a second triangular prism are mutually bonded; wherein
the first optical member and the second optical member are bonded that the surface of the first diamond-shaped prism of the first optical member and the surface of the second diamond-shaped prism of the second optical member are perpendicular.

* * * * *